United States Patent
Dette et al.

(10) Patent No.: US 9,205,197 B2
(45) Date of Patent: *Dec. 8, 2015

(54) DRUG DELIVERY DEVICE DOSE SETTING MECHANISM

(75) Inventors: Christoph Dette, Kelkheim (DE); Paul Jansen, Frankfurt (DE); Christian Pommereau, Undenheim (DE); Robert Frederick Veasey, Leamington Spa (GB); Robert Perkins, Leamington Spa (GB); David Aubrey Plumptre, Droitwich (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 865 days.

This patent is subject to a terminal disclaimer.

(21) Appl. No.: 12/357,899

(22) Filed: Jan. 22, 2009

(65) Prior Publication Data

US 2009/0264828 A1    Oct. 22, 2009

Related U.S. Application Data

(63) Continuation-in-part of application No. 11/520,598, filed on Sep. 14, 2006, now Pat. No. 7,935,088, which is a continuation of application No. 10/790,866, filed on Mar. 3, 2004, now abandoned.

(30) Foreign Application Priority Data

Mar. 3, 2003  (GB) .................................. 0304822.0

(51) Int. Cl.
*A61M 5/315* (2006.01)
*A61M 5/24* (2006.01)
(Continued)

(52) U.S. Cl.
CPC ............. *A61M 5/31551* (2013.01); *A61M 5/24* (2013.01); *A61M 5/31533* (2013.01);
(Continued)

(58) Field of Classification Search
CPC . A61M 5/31; A61M 5/24; A61M 2005/3123; A61M 2005/3125; A61M 2005/3126; A61M 2005/3154; A61M 5/31551; A61M 5/31556; A61M 5/31568; A61M 5/3157; A61M 5/31573; A61M 5/31526; A61M 5/31533; A61M 5/31535; A61M 5/31536; A61M 2205/583; A61M 2205/586
USPC .......................... 604/189, 207–211, 224, 246
See application file for complete search history.

(56) References Cited

U.S. PATENT DOCUMENTS

| 2,444,570 A | 7/1948 | Lawrence et al. |
| 4,470,317 A | 9/1984 | Sabloewski et al. |

(Continued)

FOREIGN PATENT DOCUMENTS

| DE | 3609555 | 9/1987 |
| EP | 295075 | 12/1988 |

(Continued)

OTHER PUBLICATIONS

Reissue U.S. Appl. No. 10/442,855, "Injection Syringe", Filed May 21, 2003, including as-filed specification, drawings, abstract, and claims, as well as the reissue declaration and a list of documents found as of Mar. 3, 2011.

(Continued)

*Primary Examiner* — Andrew Gilbert
(74) *Attorney, Agent, or Firm* — McDonnell Boehnen Hulbert & Berghoff LLP

(57) ABSTRACT

A method and system for proving a drug delivery device. The device comprises a drug delivery device housing and a medicament contained in the drug delivery device housing. A dose dial sleeve is positioned in the housing and is rotatable to set a non-inverted dose of the medicament contained in the medical delivery device. The non-inverted dose may be increased by turning the dose dial sleeve in a direction towards a user of the drug delivery device. The dose medicament may be decreased by rotating the dose dial sleeve in a direction away from the user.

21 Claims, 15 Drawing Sheets

(51) Int. Cl.
*A61M 5/00* (2006.01)
*A61M 5/32* (2006.01)
*A61M 5/31* (2006.01)

(52) U.S. Cl.
CPC .......... *A61M 5/31565* (2013.01); *A61M 5/002* (2013.01); *A61M 5/3156* (2013.01); *A61M 5/31535* (2013.01); *A61M 5/31575* (2013.01); *A61M 5/31585* (2013.01); *A61M 5/3202* (2013.01); *A61M 2005/2407* (2013.01); *A61M 2005/3125* (2013.01); *A61M 2005/3126* (2013.01); *A61M 2205/581* (2013.01); *A61M 2205/582* (2013.01); *A61M 2205/586* (2013.01)

(56) References Cited

U.S. PATENT DOCUMENTS

| | | |
|---|---|---|
| 4,498,904 A | 2/1985 | Turner et al. |
| 4,568,335 A | 2/1986 | Updike et al. |
| 4,585,439 A | 4/1986 | Michel |
| 4,833,379 A | 5/1989 | Kaibel et al. |
| 4,865,591 A | 9/1989 | Sams |
| 4,883,472 A | 11/1989 | Michel |
| 4,919,596 A | 4/1990 | Slate et al. |
| 4,936,833 A * | 6/1990 | Sams ............................ 604/232 |
| 4,973,318 A | 11/1990 | Holm |
| 4,994,033 A | 2/1991 | Shockey et al. |
| 5,017,190 A | 5/1991 | Simon et al. |
| 5,042,977 A * | 8/1991 | Bechtold et al. .............. 604/134 |
| 5,112,317 A | 5/1992 | Michel |
| 5,207,752 A | 5/1993 | Sorenson et al. |
| 5,226,895 A * | 7/1993 | Harris ........................... 604/208 |
| 5,226,896 A * | 7/1993 | Harris ........................... 604/211 |
| 5,246,417 A | 9/1993 | Haak et al. |
| 5,257,987 A | 11/1993 | Athayde et al. |
| 5,271,527 A | 12/1993 | Haber et al. |
| 5,279,585 A | 1/1994 | Balkwill |
| 5,279,586 A | 1/1994 | Balkwill |
| 5,281,198 A | 1/1994 | Haber et al. |
| 5,284,480 A | 2/1994 | Porter et al. |
| 5,304,152 A | 4/1994 | Sams |
| 5,308,340 A | 5/1994 | Harris |
| 5,314,412 A | 5/1994 | Rex |
| 5,318,540 A | 6/1994 | Athayde et al. |
| 5,320,609 A | 6/1994 | Haber et al. |
| 5,331,954 A | 7/1994 | Rex et al. |
| 5,370,629 A | 12/1994 | Michel et al. |
| 5,376,081 A * | 12/1994 | Sapienza ....................... 604/207 |
| 5,380,297 A | 1/1995 | Wadman et al. |
| 5,383,865 A * | 1/1995 | Michel .......................... 604/232 |
| 5,440,976 A | 8/1995 | Giuliano et al. |
| 5,445,606 A | 8/1995 | Haak et al. |
| 5,447,150 A | 9/1995 | Bacon |
| 5,478,316 A | 12/1995 | Bitdinger et al. |
| 5,480,387 A * | 1/1996 | Gabriel et al. ............... 604/134 |
| 5,492,534 A | 2/1996 | Athayde et al. |
| 5,503,628 A * | 4/1996 | Fetters et al. .................. 604/72 |
| 5,505,704 A | 4/1996 | Pawelka et al. |
| 5,514,097 A * | 5/1996 | Knauer ......................... 604/136 |
| 5,545,147 A * | 8/1996 | Harris ........................... 604/209 |
| 5,546,932 A | 8/1996 | Galli |
| 5,549,574 A | 8/1996 | Townsend |
| 5,549,575 A | 8/1996 | Giambattista |
| 5,584,815 A | 12/1996 | Pawelka |
| 5,591,136 A | 1/1997 | Gabriel |
| 5,599,314 A | 2/1997 | Neill |
| 5,611,783 A | 3/1997 | Mikkelson |
| 5,626,566 A | 5/1997 | Peterson et al. |
| 5,645,052 A | 7/1997 | Kersey |
| 5,674,204 A | 10/1997 | Chanoch |
| 5,679,111 A | 10/1997 | Hjertman et al. |
| 5,681,285 A | 10/1997 | Ford et al. |
| 5,685,864 A | 11/1997 | Shanely et al. |
| 5,688,251 A | 11/1997 | Chanoch |
| 5,692,640 A * | 12/1997 | Caulfield et al. ................ 221/70 |
| 5,693,027 A | 12/1997 | Hansen et al. |
| 5,709,662 A | 1/1998 | Olive et al. |
| 5,716,990 A | 2/1998 | Bagshawe et al. |
| 5,725,508 A | 3/1998 | Chanoch et al. |
| 5,743,889 A | 4/1998 | Sams |
| 5,755,692 A | 5/1998 | Manicom |
| 5,823,998 A | 10/1998 | Yamagata |
| 5,827,232 A | 10/1998 | Chanoch |
| 5,843,036 A | 12/1998 | Olive et al. |
| 5,882,718 A | 3/1999 | Pommer et al. |
| 5,898,028 A | 4/1999 | Jensen et al. |
| 5,921,966 A | 7/1999 | Bendek et al. |
| 5,928,201 A | 7/1999 | Poulsen et al. |
| 5,938,642 A | 8/1999 | Burroughs et al. |
| 5,947,934 A | 9/1999 | Hansen et al. |
| 5,951,530 A | 9/1999 | Steengaard et al. |
| 5,954,689 A | 9/1999 | Poulsen |
| 5,961,496 A | 10/1999 | Nielsen et al. |
| 5,980,491 A | 11/1999 | Hansen |
| 5,984,900 A | 11/1999 | Mikkelsen |
| 6,003,736 A | 12/1999 | Ljunggren |
| 6,004,297 A * | 12/1999 | Steenfeldt-Jensen et al. ............................ 604/207 |
| 6,010,485 A | 1/2000 | Buch-Rasmussen et al. |
| 6,033,376 A | 3/2000 | Rockley |
| 6,033,377 A | 3/2000 | Rasmussen et al. |
| 6,048,336 A | 4/2000 | Gabriel |
| 6,074,372 A | 6/2000 | Hansen |
| 6,083,197 A | 7/2000 | Umbaugh |
| 6,086,567 A | 7/2000 | Kirchhofer et al. |
| 6,096,010 A | 8/2000 | Walters |
| 6,110,149 A | 8/2000 | Klitgaard et al. |
| 6,129,080 A | 10/2000 | Pitcher et al. |
| 6,146,361 A | 11/2000 | DiBiasi et al. |
| 6,193,698 B1 | 2/2001 | Kirchhofer et al. |
| 6,221,046 B1 | 4/2001 | Burroughs et al. |
| 6,221,053 B1 | 4/2001 | Walters et al. |
| 6,231,540 B1 | 5/2001 | Smedegaard |
| 6,235,004 B1 * | 5/2001 | Steenfeldt-Jensen et al. ............................ 604/207 |
| 6,248,090 B1 | 6/2001 | Jensen et al. |
| 6,248,095 B1 | 6/2001 | Giambattista et al. |
| 6,258,062 B1 | 7/2001 | Thielen et al. |
| 6,269,340 B1 | 7/2001 | Ford et al. |
| 6,277,097 B1 | 8/2001 | Mikkelsen et al. |
| 6,277,098 B1 | 8/2001 | Klitmose et al. |
| 6,281,225 B1 | 8/2001 | Hearst et al. |
| 6,283,941 B1 | 9/2001 | Schoenfeld et al. |
| 6,287,283 B1 | 9/2001 | Ljunggreen |
| 6,302,869 B1 | 10/2001 | Klitgaard |
| 6,312,413 B1 | 11/2001 | Jensen et al. |
| 6,340,357 B1 | 1/2002 | Poulsen et al. |
| 6,379,339 B1 | 4/2002 | Klitgaard et al. |
| 6,454,746 B1 * | 9/2002 | Bydlon et al. ................. 604/227 |
| 6,514,230 B1 | 2/2003 | Munk et al. |
| 6,547,763 B2 | 4/2003 | Steenfeldt-Jensen et al. |
| 6,547,764 B2 | 4/2003 | Larsen et al. |
| 6,562,011 B1 | 5/2003 | Buch-Rasmussen et al. |
| 6,569,126 B1 | 5/2003 | Poulsen et al. |
| 6,582,404 B1 | 6/2003 | Klitgaard et al. |
| 6,605,067 B1 | 8/2003 | Larsen |
| 6,613,019 B2 | 9/2003 | Munk |
| 6,663,602 B2 | 12/2003 | Moller |
| 6,692,472 B2 | 2/2004 | Hansen et al. |
| 6,716,198 B2 | 4/2004 | Larsen |
| 6,726,661 B2 | 4/2004 | Munk et al. |
| 6,770,288 B2 | 8/2004 | Duirs |
| 6,796,970 B1 | 9/2004 | Klitmose et al. |
| 6,893,415 B2 | 5/2005 | Madsen et al. |
| 6,899,698 B2 | 5/2005 | Sams |
| 6,899,699 B2 | 5/2005 | Enggaard |
| 6,932,794 B2 | 8/2005 | Giambattista et al. |
| 6,936,032 B1 * | 8/2005 | Bush et al. .................... 604/187 |
| 6,945,961 B2 | 9/2005 | Miller et al. |
| 7,008,399 B2 | 3/2006 | Larsen et al. |
| 7,090,662 B2 | 8/2006 | Wimpenny et al. |
| 7,094,221 B2 | 8/2006 | Veasey et al. |
| 7,104,972 B2 | 9/2006 | Moller et al. |
| 7,133,329 B2 | 11/2006 | Skyggebjerg et al. |

(56) References Cited

U.S. PATENT DOCUMENTS

| | | | |
|---|---|---|---|
| 7,169,132 B2 | 1/2007 | Bendek et al. | |
| 7,175,055 B2 | 2/2007 | Hansen et al. | |
| 7,241,278 B2 | 7/2007 | Moller | |
| 7,291,132 B2 | 11/2007 | DeRuntz et al. | |
| 7,316,670 B2 | 1/2008 | Graf et al. | |
| 7,553,299 B2 | 6/2009 | Veasey et al. | |
| 7,935,088 B2 * | 5/2011 | Veasey et al. | 604/207 |
| 2002/0007154 A1 | 1/2002 | Hansen et al. | |
| 2002/0052578 A1 | 5/2002 | Moller | |
| 2002/0077852 A1 | 6/2002 | Ford et al. | |
| 2002/0120235 A1 * | 8/2002 | Enggaard | 604/135 |
| 2003/0039679 A1 | 2/2003 | Duirs | |
| 2003/0050609 A1 * | 3/2003 | Sams | 604/208 |
| 2003/0172924 A1 | 9/2003 | Staniforth et al. | |
| 2004/0059299 A1 | 3/2004 | Moller | |
| 2004/0127858 A1 | 7/2004 | Bendek et al. | |
| 2004/0186431 A1 | 9/2004 | Graf et al. | |
| 2004/0210199 A1 | 10/2004 | Atterbury et al. | |
| 2004/0236282 A1 | 11/2004 | Braithwaite | |
| 2004/0249348 A1 | 12/2004 | Wimpenny et al. | |
| 2004/0260247 A1 | 12/2004 | Veasey et al. | |
| 2004/0267207 A1 | 12/2004 | Veasey et al. | |
| 2004/0267208 A1 | 12/2004 | Veasey et al. | |
| 2005/0004529 A1 | 1/2005 | Veasey et al. | |
| 2005/0019400 A1 | 1/2005 | Deveney et al. | |
| 2005/0033244 A1 | 2/2005 | Veasey et al. | |
| 2005/0055011 A1 | 3/2005 | Enggaanrd | |
| 2005/0113765 A1 | 5/2005 | Veasey et al. | |
| 2005/0205083 A1 | 9/2005 | Staniforth et al. | |
| 2005/0209570 A1 | 9/2005 | Moller | |
| 2005/0268915 A1 | 12/2005 | Wassenaar et al. | |
| 2006/0206057 A1 | 9/2006 | DeRuntz et al. | |
| 2006/0264839 A1 | 11/2006 | Veasey et al. | |
| 2007/0093761 A1 | 4/2007 | Veasey et al. | |
| 2008/0188814 A1 * | 8/2008 | Lavi-Loebl et al. | 604/189 |
| 2009/0275915 A1 * | 11/2009 | Harms | A61M 5/31551 604/506 |

FOREIGN PATENT DOCUMENTS

| | | |
|---|---|---|
| EP | 327910 | 8/1989 |
| EP | 359070 B1 | 3/1990 |
| EP | 450905 | 10/1991 |
| EP | 498737 | 8/1992 |
| EP | 554996 | 8/1993 |
| EP | 594349 | 4/1994 |
| EP | 608343 B1 | 8/1994 |
| EP | 702970 | 3/1996 |
| EP | 0673482 | 4/1998 |
| EP | 879610 | 11/1998 |
| EP | 0937471 | 8/1999 |
| EP | 0937476 | 8/1999 |
| EP | 1250167 B1 | 7/2005 |
| EP | 1294418 | 7/2005 |
| EP | 1570876 A2 | 7/2005 |
| FR | 2583291 | 12/1986 |
| FR | 2767479 | 2/1999 |
| GB | 735443 | 8/1955 |
| GB | 1232899 | 5/1971 |
| GB | 2141799 | 1/1985 |
| JP | 05337179 | 12/1993 |
| JP | 06296691 | 10/1994 |
| RU | 2111019 | 5/1998 |
| WO | 8907463 | 8/1989 |
| WO | 9009202 | 8/1990 |
| WO | 9110460 | 7/1991 |
| WO | 9114467 | 10/1991 |
| WO | 9307922 | 4/1993 |
| WO | 9419034 | 9/1994 |
| WO | 9626754 | 9/1996 |
| WO | 9638190 | 12/1996 |
| WO | 9736626 | 10/1997 |
| WO | 9810813 | 3/1998 |
| WO | 9856436 | 12/1998 |
| WO | 9857688 | 12/1998 |
| WO | 9916487 | 4/1999 |
| WO | 9938554 | 8/1999 |
| WO | 9938554 A1 | 8/1999 |
| WO | 0119434 | 3/2001 |

OTHER PUBLICATIONS

Reissue U.S. Appl. No. 10/960,900, "Injection Syringe", Filed Oct. 7, 2004, including as-filed specification, drawings, abstract, and claims, as well as the reissue declaration and a list of documents found as of Mar. 3, 2011.

Reissue U.S. Appl. No. 11/121,331, "Injection Syringe", Filed Dec. 18, 2006, including as-filed specification, drawings, abstract, and claims, as well as the reissue declaration and a list of documents found as of Mar. 3, 2011.

Reissue U.S. Appl. No. 11/640,610, "Injection Syringe", Filed May 3, 2005, including as-filed specification, drawings, abstract, and claims, as well as the reissue declaration and a list of documents found as of Mar. 3, 2011.

US Office Action mailed Mar. 14, 2006 in U.S. Appl. No. 10/790,866.
US Office Action mailed Dec. 18, 2008 in U.S. Appl. No. 10/960,600.
US Office Action mailed Apr. 17, 2009 in U.S. Appl. No. 11/121,331.
US Office Action mailed Apr. 17, 2009 in U.S. Appl. No. 11/640,610.

* cited by examiner

DRUG DELIVERY DEVICE DOSE SETTING MECHANISM

RELATED APPLICATION

The present application is a continuation in part application of U.S. patent application Ser. No. 11/520,598 filed on Sep. 14, 2006, now U.S. Pat. No. 7,935,088, which is a continuation of U.S. patent application Ser. No. 10/790,866 filed on Mar. 3, 2004, now abandoned, which claims priority under 35 U.S.C. §119(b) to foreign application GB 0304822.0 filed on Mar. 15, 2004 which are entirely herein incorporated by reference and to which the reader is directed for further information.

BACKGROUND

1. Field of the Present Patent Application

The present patent application is generally directed to dose setting mechanisms for drug delivery devices. More particularly, the present patent application is generally directed to drug delivery devices, such as pen type drug delivery devices. Such devices provide for self administration of medicinal product from a multi-dose cartridge and permit a user to set the delivery dose. The present application may find application in both disposable and reusable type drug delivery devices. However, aspects of the invention may be equally applicable in other scenarios as well.

2. Background

Pen type drug delivery devices have application where regular injection by persons without formal medical training occurs. This is increasingly common among patients having diabetes where self-treatment enables such patients to conduct effective management of their disease.

Diabetes has been shown to cause certain problems. For example, people with diabetes can get high blood pressure, kidney disease, nerve damage, heart disease, and even in certain circumstances blindness. The damage caused by these problems may occur in patients whose blood sugar has been out of control for years. Keeping blood sugar under control, by way of effective insulin administration, is one method that can help prevent this damage from occurring.

In addition, people with diabetes can go into "diabetic coma" if their blood sugar is too high. They can also develop blood sugar that is too low (i.e, hypoglycemia) if they don't get enough food, or they exercise too much without adjusting insulin or food. Both diabetic coma and hypoglycemia can be very serious, and even fatal, if not treated quickly. Closely watching blood sugar, being aware of the early signs and symptoms of blood sugar that is too high or too low, and treating those conditions early can prevent these problems from becoming too serious.

Pen type drug delivery devices have been designed and developed to help patients suffering from diabetes so as to prevent such problems from occurring. The circumstances identified above highlight a number of design considerations and criteria for drug delivery devices, especially those that may be used to treat diabetes. As just one example, one requirement is that the drug delivery device must be robust in construction. The drug delivery device must also be easy to use both in terms of the drug delivery device manipulation and understanding of the device's operation. Diabetics have to inject themselves repeatedly with insulin solution and the volume of insulin to be injected may vary from patient to patient and even from injection to injection. For at least this reason, certain diabetics may require drug delivery devices that allow the patient to inject successive measured dosages of the same or perhaps different preset volumes of insulin solution accurately and with minimum dexterity challenges. This presents a further design challenge since, in the case of certain diabetics, users may have impaired vision and/or may be physically infirm with limited dexterity.

The problem of a patient's impaired vision and limited dexterity is further exacerbated by drug delivery devices that force a patient to use his or her less dominant hand. In other words, people suffering from diabetes who prefer to use their left hand (i.e., left handed patients) have an even greater desire or need for a drug delivery device that takes this user preference into consideration so that the patient is no longer forced to use his or her less dominant or weaker hand.

For example, certain studies suggest that approximately ten percent of the adult population is left-handed. It is also generally known that these left-handed individuals are sometimes placed at a disadvantage by the prevalence of right-handed tools and devices, such as medical drug delivery devices. Many tools and drug delivery devices are designed to be comfortably used with a user's right hand but not the user's left hand. As just one example, right-handed scissors, are arranged so that the line being cut along can be seen by a right-handed user, but is obscured to a left-handed user. Furthermore, the handles of these scissors are often molded in a way that is difficult or uncomfortable to be held by a left-handed user. Consequently, extensive use in such cases can lead to varying levels of efficiency and/or discomfort. As just another example of the right handed nature of tools and devices, the computer mouse is sometimes made to fit the right hand better than the left hand.

Consequently, with respect to the use of drug devices, many left handed patients, especially those already suffering from certain limitations such as partial blindness and limited dexterity, are further facing a heightened challenge when using a right-handed drug delivery device. These patients are being forced to use their less dominant hand to manipulate certain drug delivery devices, many of which have complicated dose setting and injection operations. This may be especially true where the left handed patient must user his or her less dominant right hand to manipulate the device to set an accurate dose of medicine (such as insulin) and then also inject a dose of medicine. As already mentioned above, inaccurate dose setting or injection of certain self administered drugs, such as insulin, could lead to fatal results.

There is, therefore, a general need to take these left handed and right handed issues into consideration in the design and development of drug delivery devices. Such drug delivery devices would allow a user to use his or her more dominant hand (their left hand) to set and then inject an accurate dose of medication.

SUMMARY

According to an exemplary embodiment, a drug delivery device comprises a drug delivery device housing and a medicament contained in said drug delivery device housing. A dose dial sleeve is positioned in said housing and rotatable to set a non-inverted dose of said medicament contained in said medical delivery device. Said non-inverted dose may be increased by turning said dose dial sleeve in a direction towards a user of said drug delivery device. With the drug delivery, said dose of said medicament may be decreased by rotating said dose dial sleeve in a direction away from said user.

In an alternative arrangement, a pen type drug delivery device comprises a drug delivery device housing. The housing having a distal end for mounting a needle assembly and a proximal end comprising a dose dial grip. A cartridge is contained in said housing, said cartridge containing a medication. A dose dial sleeve is rotatably mounted and operatively coupled to said dose dial grip. The dose dial grip may be rotated in a direction towards a user to set a dose. As said dose dial grip is rotated, both said dose dial grip and said dose dial sleeve translate away from said proximal end of said drug delivery housing. A non-inverted scale viewable in a window of said housing is representative of said dose. In this drug delivery device, said dose may be increased by turning said dose dial grip in a direction towards said user.

These as well as other advantages of various aspects of Applicants' proposed drug delivery device will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1:
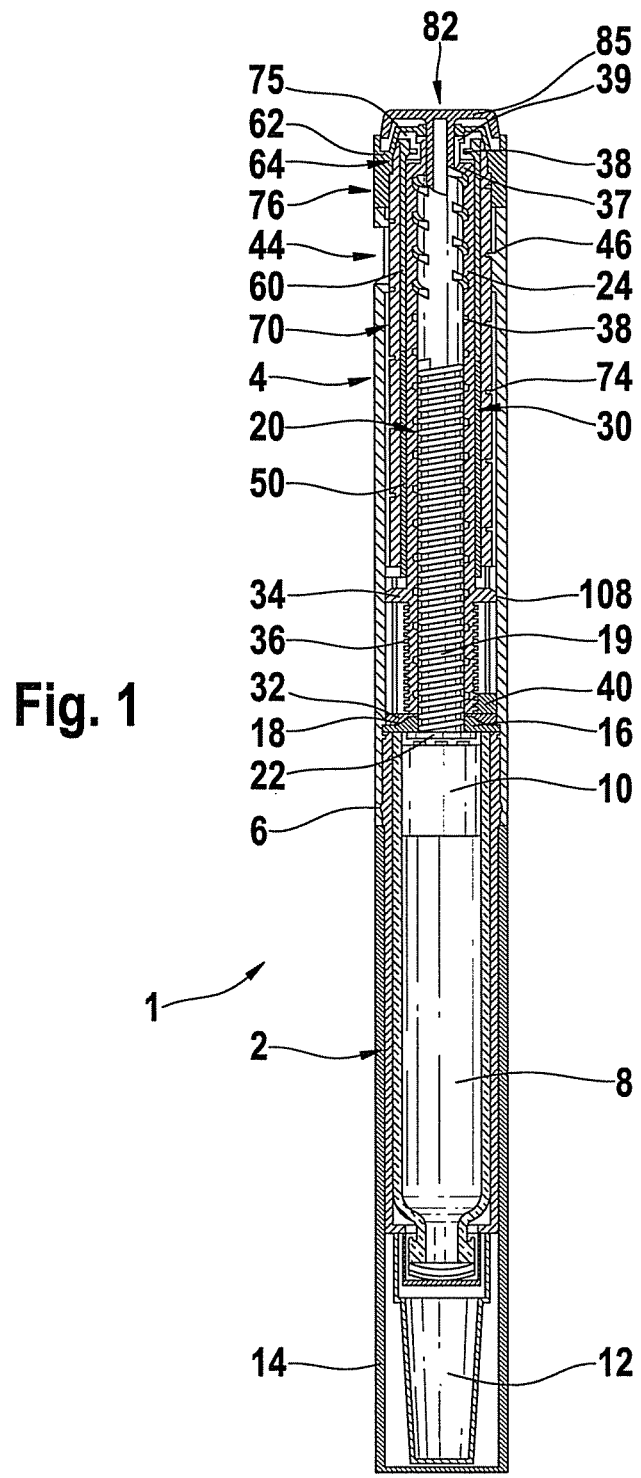
FIG. 1 illustrates a sectional view of a first embodiment of the drug delivery device in accordance with the one arrangement of the device in a first, cartridge full, position.
Figure 2:
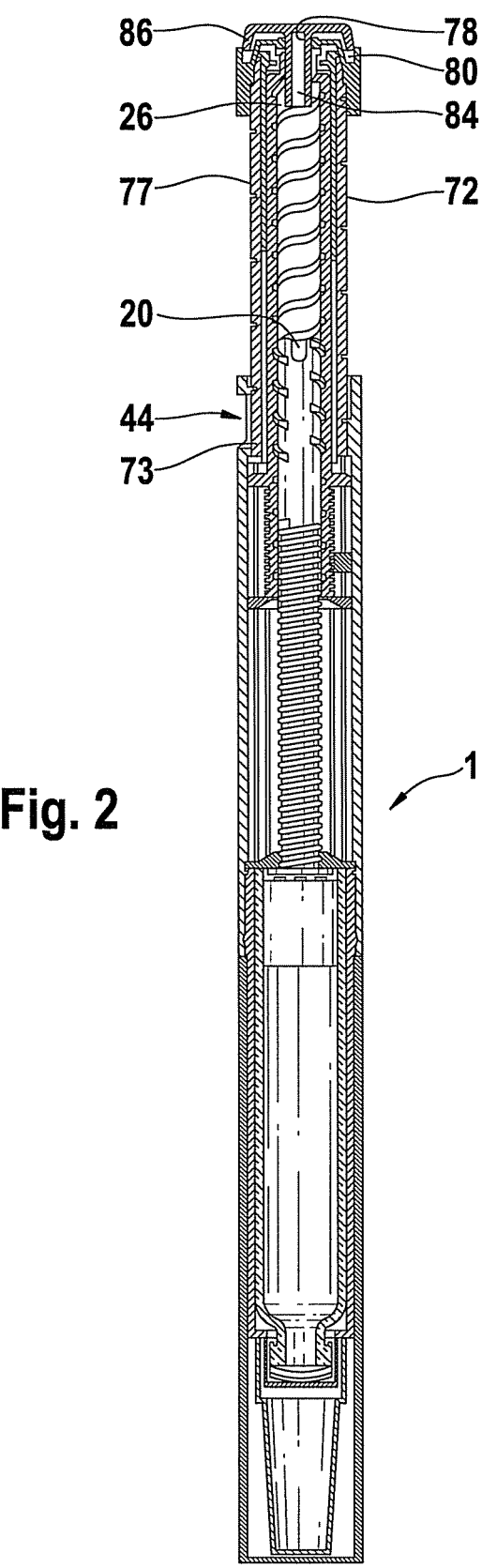
FIG. 2 illustrates a sectional view of the drug delivery device of FIG. 1 in a second, maximum first dose dialed, position.
Figure 3:
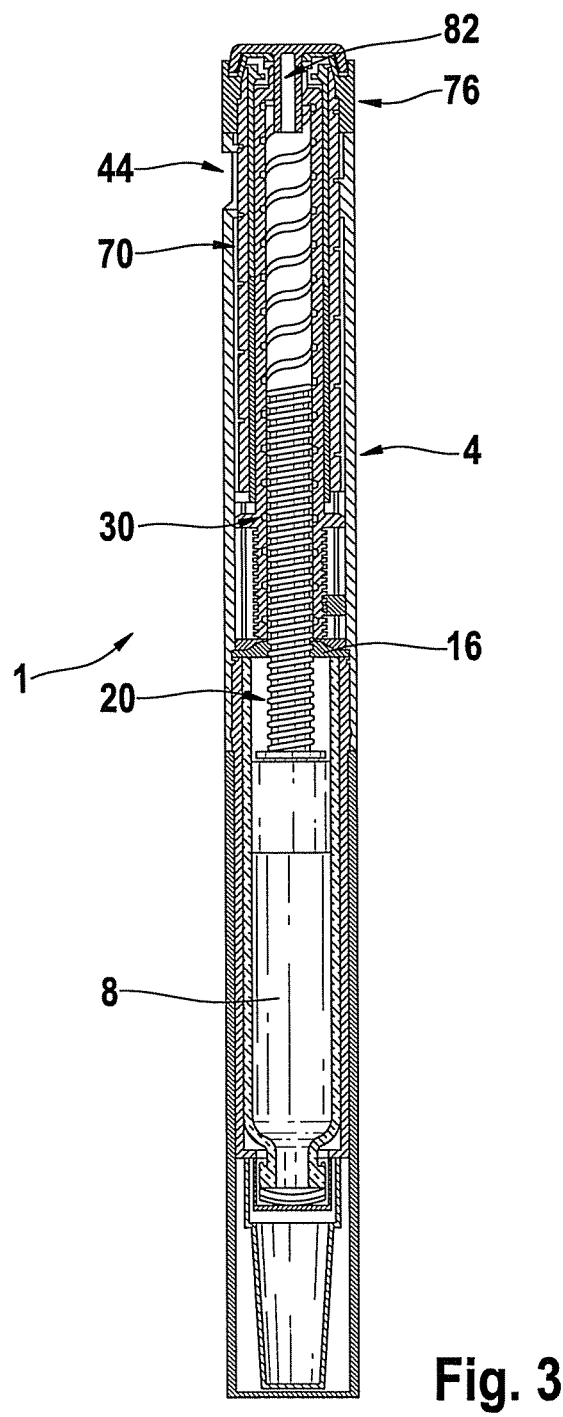
FIG. 3 illustrates a sectional view of the drug delivery device of FIG. 1 in a third, maximum first dose dispensed, position.
Figure 4:
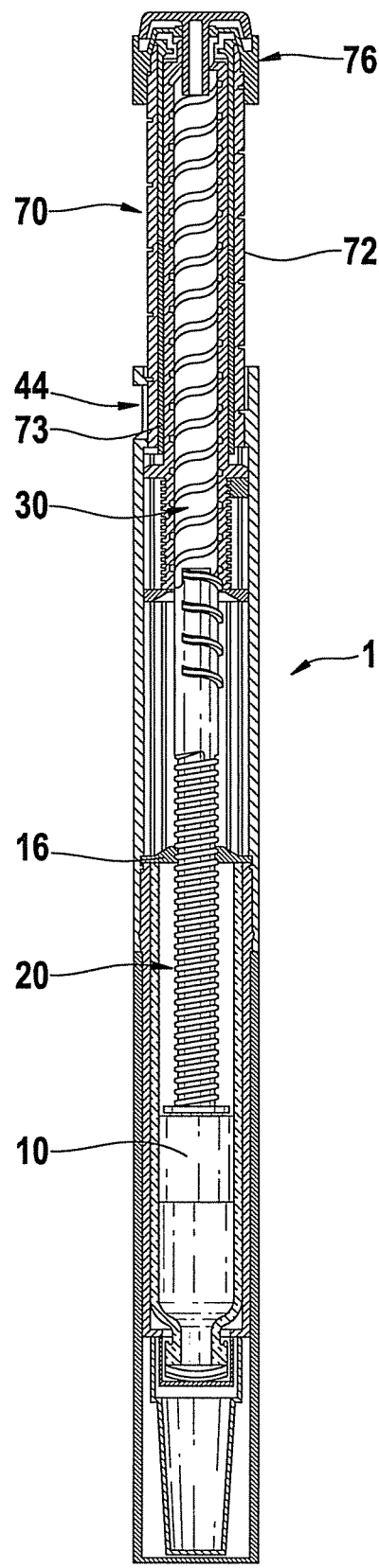
FIG. 4 illustrates a sectional view of the drug delivery device of FIG. 1 in a fourth, final dose dialed, position.
Figure 5:
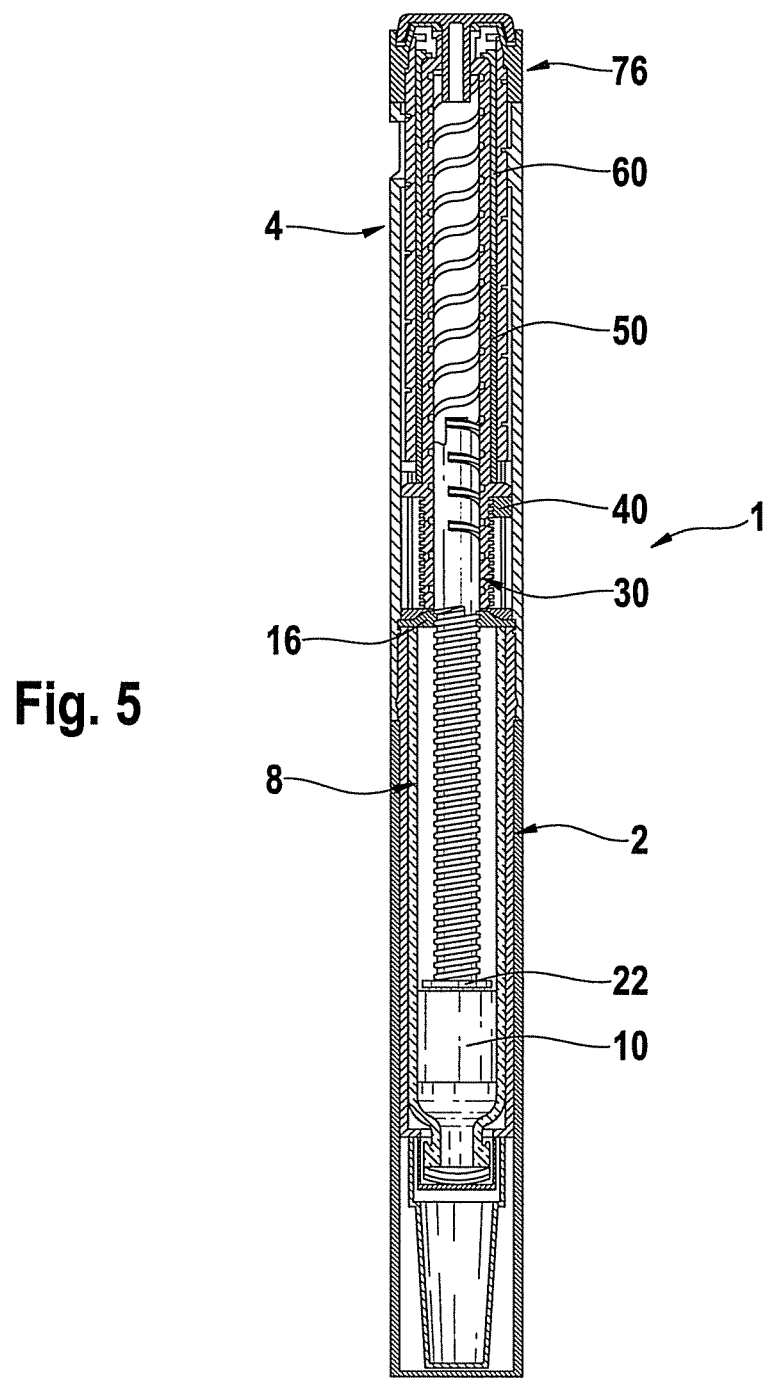
FIG. 5 illustrates a sectional view of the drug delivery device of FIG. 1 in a fifth, final dose dispensed, position.

Referring first to FIGS. 1 to 5, there is shown a drug delivery device 1 in accordance with the one arrangement in a plurality of operating positions: for dose setting and for dose administration or injection. The drug delivery device 1 comprises a housing having a first cartridge retaining part 2, and second main (exterior) housing part 4. A first end of the cartridge retaining means 2 and a second end of the main housing 4 are secured together by retaining features 6. In this illustrated arrangement, the cartridge retaining means 2 is secured within the second end of the main housing 4.

A cartridge 8 from which a number of doses of a medicinal product may be dispensed is provided in the cartridge retaining part 2. Preferably, the cartridge contains a type of medicament that must be administered often, such as once or more times a day. One such medicament is insulin. A piston 10 is retained in a first end of the cartridge. A removable cap 12 is releasably retained over a second end of the cartridge retaining part 2.

The dose setting mechanism of the drug delivery device illustrated in FIGS. 1-5 may be utilized as either a disposable or reusable drug delivery device. Where the drug delivery device comprises a disposable drug delivery device, the cartridge cannot be removed from the device without destroying the device. Alternatively, where the drug delivery device comprises a reusable drug delivery device, the cartridge is removable and may be removed from the device without destroying the device. In the drug delivery device 1 illustrated in FIGS. 1-5, this drug delivery device is illustrated as a disposable drug delivery. However, those of ordinary skill in the art will recognize that the dose setting mechanism could also be used on reusable drug delivery devices as well.

In use, the removable cap 12 can be replaced by a user with a suitable needle unit (not shown). Such needle unit may be screwed onto a distal end of the housing or alternatively may be snapped onto this distal end. A replaceable cap 14 is used to cover the cartridge retaining part 2 extending from the main housing 4. Preferably, the outer dimensions of the replaceable cap 14 are similar or identical to the outer dimensions of the main housing 4 so as to provide an impression of a unitary whole when the replaceable cap 14 is in position covering the cartridge retaining part 2. In the illustrated arrangement, an insert 16 is provided at a first end of the main housing 4. The insert 16 is secured against rotational or longitudinal motion. The insert 16 is provided with a threaded circular opening 18. Alternatively, the insert may be formed integrally with the main housing having the form of a radially inwardly directed flange having an internal thread.

A first helical groove 19 extends from a first end of a piston rod 20. In one arrangement, the piston rod 20 is of generally circular in cross section however other arrangements may also be used. The first end of the piston rod 20 (a distal end of the piston rod 20) extends through the threaded opening 18 in the insert 16. A pressure foot 22 is located at the first end or distal end of the piston rod 20. The pressure foot 22 is disposed to abut a second end of the cartridge piston 10. A second helical groove 24 extends 15 from a second end of the piston rod 20 (a proximal end). In the illustrated arrangement, the second helical groove 24 extends from a second end or proximal end of the piston rod 20.

In the illustrated arrangement, the second helical groove 24 comprises a series of part helical grooves rather than a complete helical groove. One advantage of this illustrated arrangement is that it is generally easier to manufacture and helps to reduce the overall force required for a user to actuate the device when dispensing the medicinal product from the drug delivery device 1.

The first helical groove 19 and the second helical groove 24 are oppositely disposed, i.e., the grooves are of opposite hand. The second end of the piston rod 20 (i.e., the proximal end of the piston rod 20) is provided with a receiving recess 26. A drive sleeve 30 extends about the piston rod 20. The drive sleeve 30 is generally cylindrical. The drive sleeve 30 is provided at a first end with a first radially extending flange 32. A second radially extending flange 34 is provided spaced a distance along the drive sleeve 30 from the first flange 32. An intermediate helical groove 36 is provided on an outer part of the drive sleeve 30 extending between the first flange 32 and the second flange 34. A helical groove 38 extends along the internal surface of the drive sleeve 38. The second helical groove 24 of the piston rod 20 is adapted to work within the helical groove 38.

A first end of the first flange 32 is adapted to conform to a second side of the insert 16. A part nut 40 is located between the drive sleeve 30 and the main housing 2, disposed between the first flange 32 and the second flange 34. In the illustrated arrangement, the part nut 40 comprises a half-nut. The part nut 40 has an internal helical groove matching the intermediate helical groove 38 of the drive sleeve 30. In one preferred arrangement, the outer surface of the part nut 40 and an internal surface of the main 5 housing 4 are keyed together by way of splines 42 (See, also FIGS. 10, 11, 15 and 16) to prevent relative rotation between the part nut 40 and the main housing 4, while allowing relative longitudinal in movement between these two components.

A shoulder 37 is formed between a second end of the drive sleeve 30 (a proximal end of the drive sleeve 30) and an extension 38 provided at the second end of the drive sleeve 30 (a distal end of the drive sleeve 30). The extension 38 has reduced inner and outer diameters in comparison to the remainder of the drive sleeve 30. A second end of the extension 38 is provided with a radially outwardly directed flange 39. As described in greater detail below, clicker 50 and a clutch 60 are disposed about the drive sleeve 30, between the drive sleeve 30 and a dose dial sleeve 70.

Figure 6:
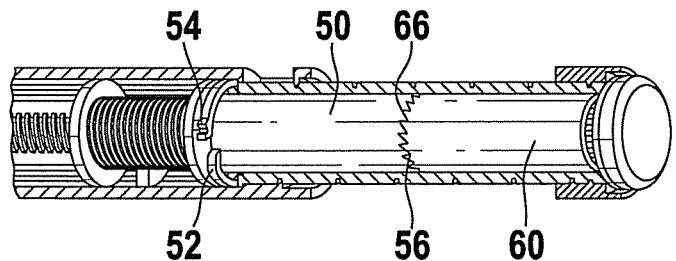
FIG. 6 illustrates a cut-away view of a first detail of the drug delivery device of FIG. 1.
Figure 7:
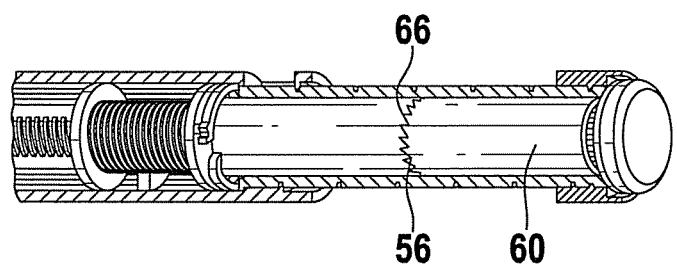
FIG. 7 illustrates a partially cut-away view of a second detail of the drug delivery device of FIG. 1.

The clicker 50 is located adjacent the second flange 34 of the drive sleeve 30. The clicker 50 is generally cylindrical and is provided at a first end with a flexible helically extending arm 52 (See, e.g., FIG. 6). A free end of the arm 52 is provided with a radially directed toothed member 54. A second end of the clicker 50 is provided with a series of circumferentially directed saw teeth 56 (FIG. 7). Each saw tooth comprises a longitudinally directed surface and an inclined surface.

In an alternative arrangement, the clicker further includes at least one spring member. The at least one spring member assists in the resetting of the clutch 60 following dispense of a previously set amount of medicament. The clutch 60 is located adjacent the second end of the drive sleeve 30. The clutch 60 is generally cylindrical and is provided at a first end (a distal end) with a series of circumferentially directed saw teeth 66 (See, e.g., FIG. 7). Each saw tooth comprises a longitudinally directed surface and an inclined surface. Towards the second end 64 (a proximal end) of the clutch 60 there is located a radially inwardly directed flange 62. The flange 62 of the clutch 60 is disposed between the shoulder 37 of the drive sleeve 30 and the radially outwardly directed flange 39 of the extension 38.

Figure 8:
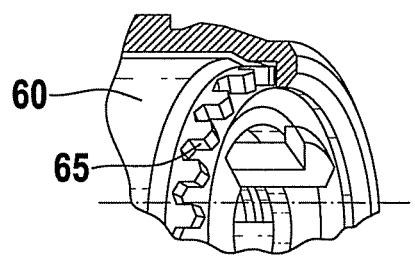
FIG. 8 illustrates a partially cut-away view of a third detail of the drug delivery device of Figure.

The second end of the clutch 60 is provided with a plurality of dog teeth 65 (See, e.g., FIG. 8). The clutch 60 is keyed to the drive sleeve 30 by way of splines (not shown) to prevent relative rotation between the clutch 60 and the drive sleeve 30. In one preferred arrangement, the clicker 50 and the clutch 60 each extend approximately half the length of the drive sleeve 30. However, it will be understood by those of ordinary skill in the art that other arrangements regarding the relative lengths of these parts are possible. The clicker 50 and the clutch 60 are engaged as shown in FIGS. 6 and 7, for example.

A dose dial sleeve 70 is provided outside of the clicker 50 and clutch 60 and radially inward of the main housing 4. The dose dial sleeve 70 comprises a distal end 73 and a proximal end 77. A helical groove 74 is provided about an outer surface 72 of the dose dial sleeve 70. The main housing 4 is provided with a window 44 through which a part of an outer surface 72 of the dose dial sleeve 70 may be viewed.

The main housing 4 is further provided with a helical rib 46, adapted to be seated in the helical groove 74 on the outer surface of the dose dial sleeve 70. In one preferred arrangement, the helical rib 46 extends for a single sweep of the inner surface of the main housing 4. A first stop is provided between the splines 42 and the helical rib. A second stop, disposed at an angle of 180" to the first stop, is formed by a frame surrounding the window 44 in the main housing 4.

Returning to FIGS. 1-5, a dose dial grip 76 is disposed about an outer surface of the second end of the dose dial sleeve 70. An outer diameter of the dose dial grip 76 preferably corresponds to the outer diameter of the main housing 4. The dose dial grip 76 is secured to the dose dial sleeve 70 to prevent relative movement between these two components. The dose dial grip 76 is provided with a central opening 78. An annular recess 80 located in the second end of the dose dial grip 76 extends around the opening 78. A button of generally 'T' section is provided at a second end of the device. A stem 84 of the 85 button may extend through the opening 78 in the dose did grip 76, through the inner diameter of the extension 38 of the drive sleeve 30 and into the receiving recess 26 at the proximal end of the piston rod 20. The stem 84 is retained for limited axial movement in the drive sleeve 30 and against rotation with respect thereto. A head 85 of the button 82 is generally circular. A skirt 86 depends from a periphery of the head 85. The skirt 86 is adapted to be seated in the annular 10 recess 80 of the dose dial grip 76.

Figure 9:
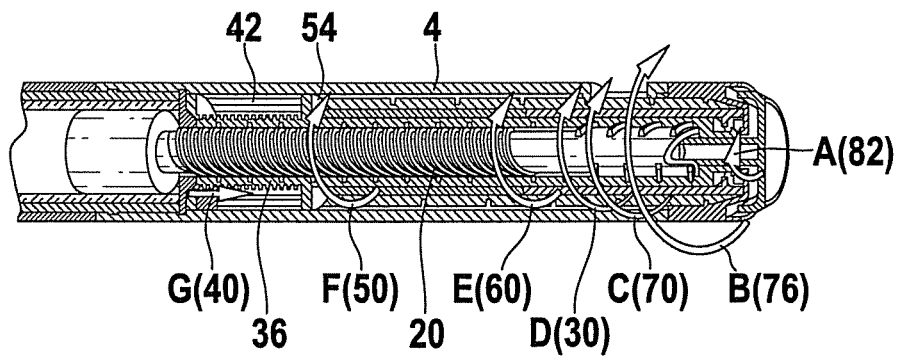
FIG. 9 illustrates a first relative movement of parts of the drug delivery device shown in FIG. 1 during dialing up of a dose.
Figure 10:
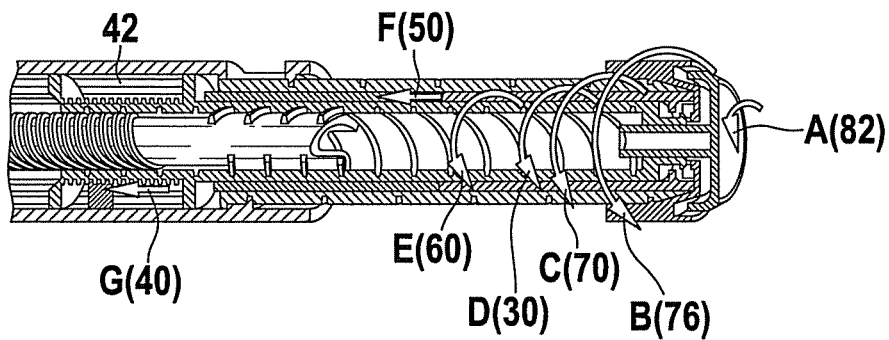
FIG. 10 illustrates the relative movement of parts of the drug delivery device shown in FIG. 9 during dialing down of a dose.
Figure 11:
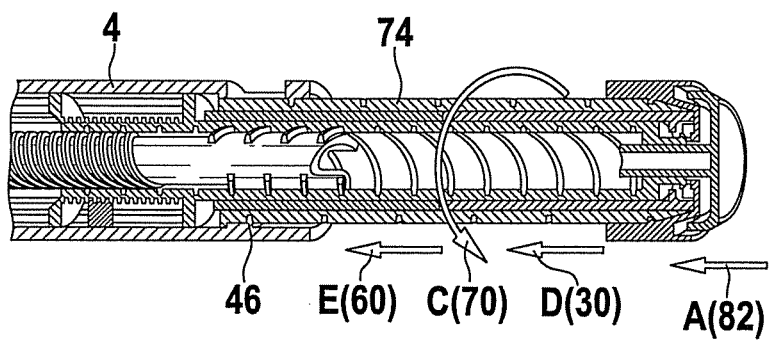
FIG. 11 illustrates the relative movement of parts of the drug delivery device shown in FIG. 9 during dispensing of a dose.

Operation of a right handed drug delivery device in accordance with a preferred arrangement will now be described. In FIGS. 9, 10 and 11 arrows, A, B, C, D, E, F and G represent the respective movements of the button 82, the dose dial grip 76, the dose dial sleeve 70, the drive sleeve 30, 15 the clutch 60, the clicker 50 and the part nut 40 in one arrangement.

Figure 15:
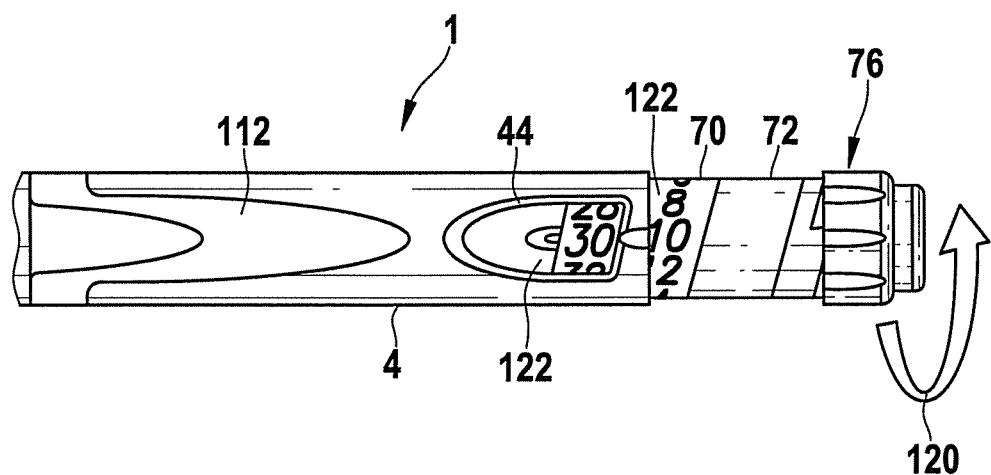
FIG. 15 illustrates how a right handed user would set a dose with the drug delivery device of FIG. 1.

To dial a dose in the arrangement illustrated in FIG. 9, a user holds the main housing 4 in his or her left hand and uses the right hand to rotate the dose dial grip 76 (arrow B) in a direction away from the user. This is also shown in FIG. 15 where the user uses his or her right hand to turn the dose dial grip 76 in the direction of arrow 120: in a direction away from the user. With the clicker 50 and clutch 60 engaged, the drive sleeve 30, the clicker 50, the clutch 60 and the dose dial sleeve 70 rotate with the dose dial grip 76 towards the user. Audible and tactile feedback of the dose being dialed is provided by the clicker 50 and the clutch 60. Torque is transmitted through the saw teeth 56, 66 between the clicker 50 and the clutch 60. The flexible arm 52 deforms and drags the toothed member 54 over the splines 42 to produce a click. Preferably, the splines 42 are disposed such that each click corresponds to a conventional unit dose, or the like.

Figure 12:
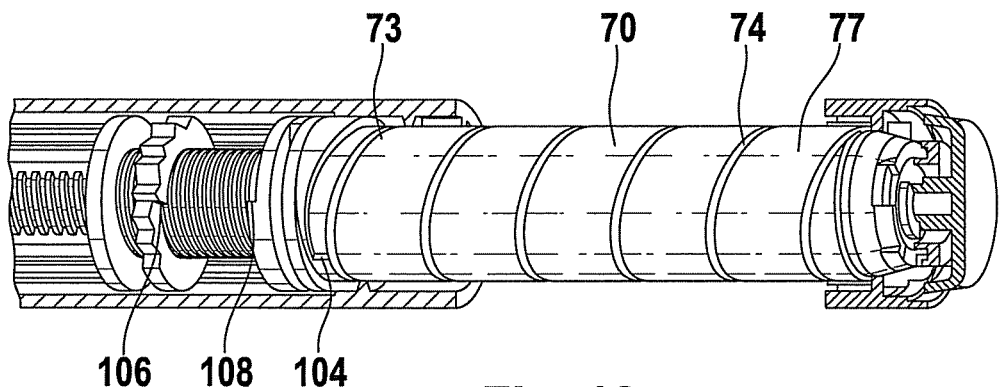
FIG. 12 illustrates a partially cut-away view of the drug delivery device of FIG. 1 in the second, maximum first dose dialed, position.

The helical groove 74 on the dose dial sleeve 70 and the helical groove 38 in the drive sleeve 30 have the same lead. This allows the dose dial sleeve 70 (arrow C) to extend in a proximal direction away from the main housing 4 (See, also FIG. 15). In this manner, the drive sleeve 30 (arrow D) climbs the piston rod 20 at the same rate. At the limit of travel, a radial stop 104 (See, e.g., FIG. 12) on the dose dial sleeve 70 engages either the first stop 100 or the second stop 102 provided on the main housing 4 to prevent further movement. Rotation of the piston rod 20 is prevented due to the opposing directions of the overhauled and driven threads on the piston rod 20. The part nut 40, keyed to the main housing 4, is advanced along the intermediate thread 36 by the rotation of the drive sleeve 30 (arrow D).

Figure 14:
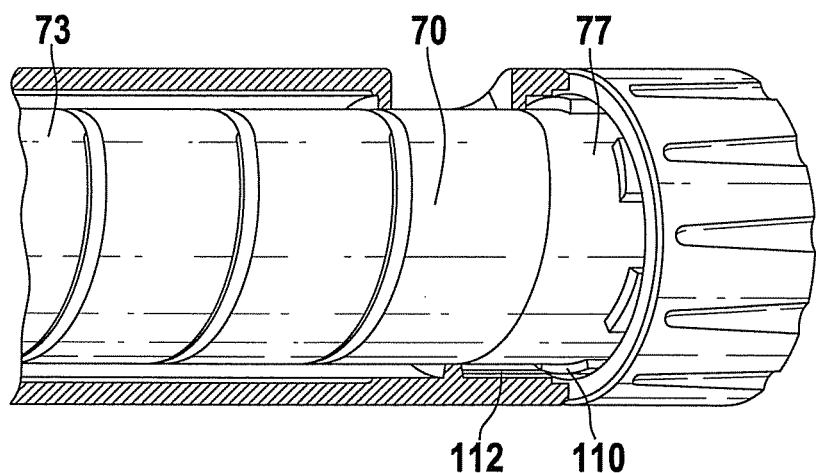
FIG. 14 illustrates a partially cut-away view of the drug delivery device of FIG. 1 in one of the first, third or fifth positions.
Figure 17:
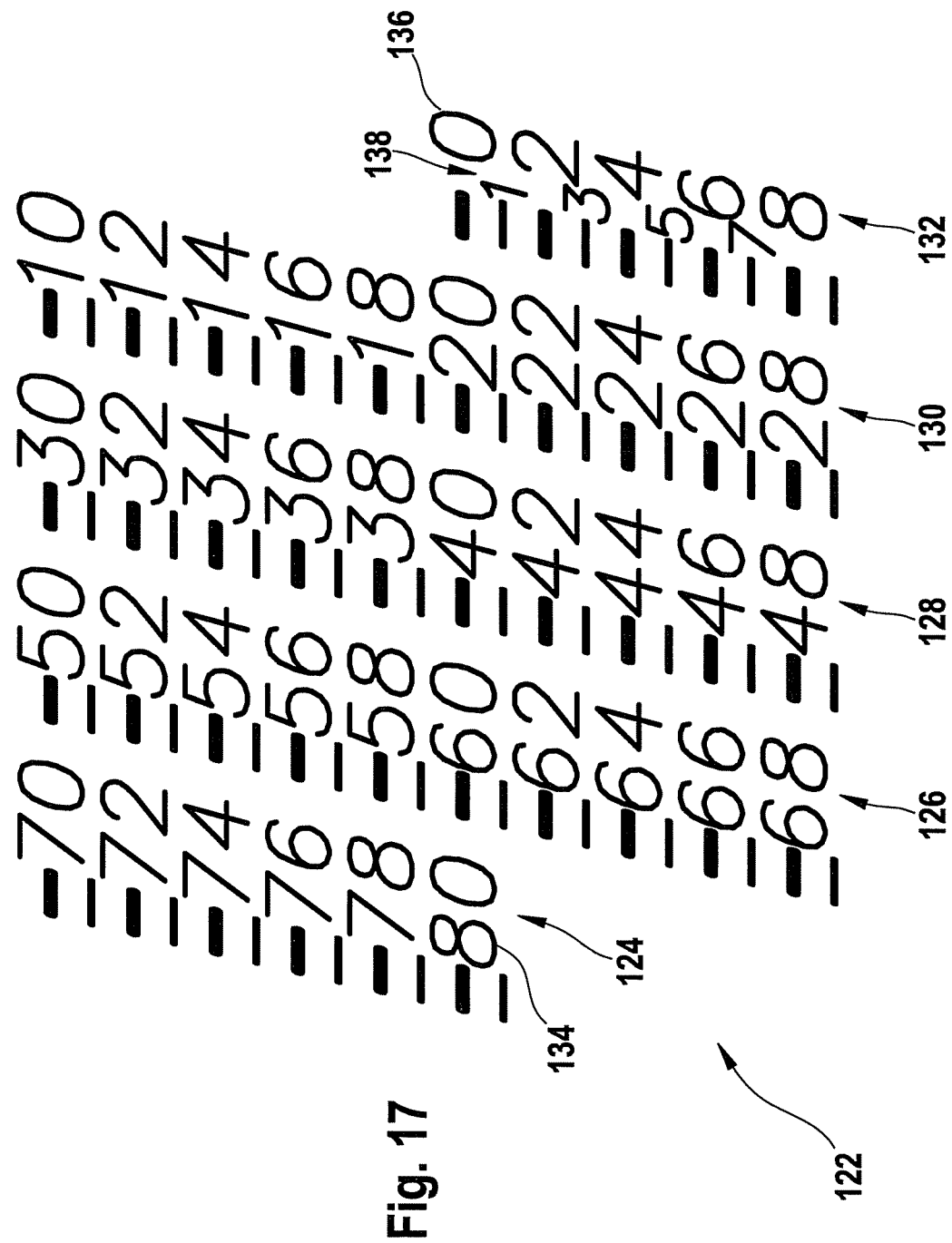
FIG. 17 illustrates a scale arrangement that might be used for the drug delivery device of FIG. 1.

A visual indication of the dose that may be dialed, for example reference numerals or a scale, may be provided on the outer surface 72 of the dose dial sleeve 70. (See, e.g., FIGS. 12 and 14) For example, FIG. 17 illustrates a first scale arrangement 122 that could be provided on the dose dial sleeve outer surface 72. In the scale arrangement 122 illustrated in FIG. 17, the arrangement 122 comprises five (5) columns of numerals: first column 124, second column 126, third column 128, fourth column 130, and fifth column 132. In each column, the column of numerals decrease by a factor of two as one proceeds up the column. For example, in first column 124 located on the left hand side of arrangement 122, first column 124 begins with the reference numeral "80" and decreases by a factor of two for each other numeral provided in this column (i.e, 80 Units then 78 Units then 76 Units, etc.).

This first scale arrangement 122 could provide a user certain visual indication through drug delivery device window 44 as the amount of dosage that a user sets. As may be seen from this first scale arrangement 122 provided in FIG. 17, a maximum scale reference numeral "80" 134 is provided at a bottom of the first column 124 and a minimum scale reference numeral "0" 136 is provided at the top of the fifth column 132. With this scale arrangement 122, the maximum settable dose by the drug delivery device 1 is "80" Units 134 and the minimum settable dose is "0" Units 136. Between the maximum and minimum reference numerals 124, 136, respectively, other doses are noted in increments of 2: (e.g., 2, 4, 6, 8 etc.). Single unit doses and odd unit doses may also be set and these are provided by way of plurality of scale marks provided between even numbered reference numerals. For example, half scale mark ("1" Units) 138 is provided between the minimum settable dose "0" Units 136 and 2 Units at the top of column 132.

Figure 18:
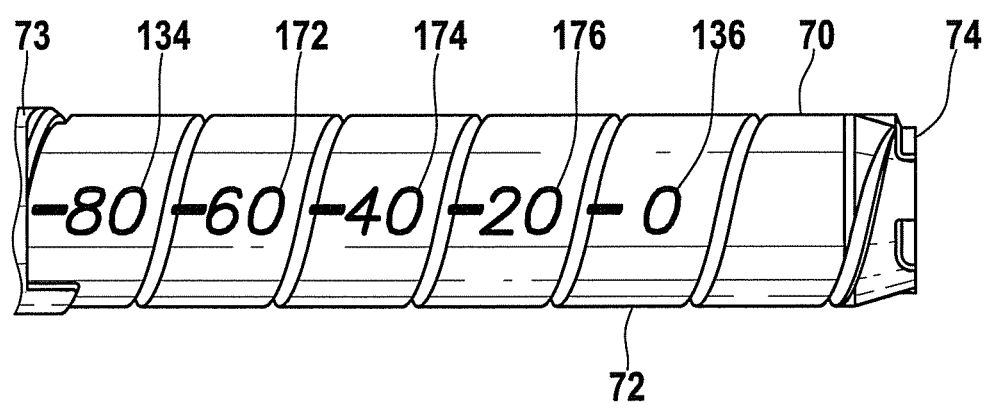
FIG. 18 illustrates the scale arrangement of FIG. 17 provided along an outer surface of a dose dial sleeve.

As may be also seen from this first scale arrangement 122, the reference numerals increase going from a right hand side of the scale 122 or the fifth scale arrangement column 132 proceeding to the left side of scale 122 (towards the first scale arrangement column 124). FIG. 18 illustrates the scale arrangement of FIG. 17 provided along an outer surface 72 of the dose dial sleeve 70. As can be seen from FIG. 18, scale arrangement 122 has the maximum settable dose value "80" provided at the distal end 73 and the minimum settable dose value "0" provided at the proximal end 74 of the dose dial sleeve 70. Intermittent scale numerals "60" Units 172, "40" Units 176 and "20" Units 178 are also provided.

Consequently, if scale arrangement 122 were provided on the dose dial sleeve 70 illustrated in FIGS. 1-5, as a user rotates the dose dial sleeve 70 by way of the dose dial grip 76 in a direction away from the user to set a dose with the user's right hand as illustrated in FIGS. 9 and 15, the dose dial sleeve 70 would extend out of the housing. For example, in FIG. 15, a user has set a dose of 30 Units with his or her right hand.

As shown in FIG. 15, as a user rotates the dose dial grip 76 and therefore the dose dial sleeve 70 in a direction away from the user (this direction illustrated by arrow 120), the scale arrangement 122 of FIG. 17 provided along an outer drum of the dose dial sleeve 70 and are consequently readable in an upright orientation by way of window 44.

Consequently, as the user uses his or right hand to rotate this dose dial sleeve, the user will receive correct visual confirmation of at least two important items: (1) the amount of the dose viewable by way of the window 44, and (2) other indication (from label 112) that a drug delivery device provider may include on the housing. For example, label 112 could include: a description of the medicament provided in the drug delivery device, an expiration date of the medication, some type of color designation of the type of medicament provided, or some type of color designation of the type of drug delivery device provided. As just one example, the drug delivery device label 112 could provide a color indication of the type of insulin provided in the drug delivery device (e.g., long acting or short acting insulin) and/or could indicate that the drug delivery device is intended for right-handed or left-handed diabetics. That is, those diabetics who tend to favor their left hand to set a dose and/or inject a dose.

Figure 13:
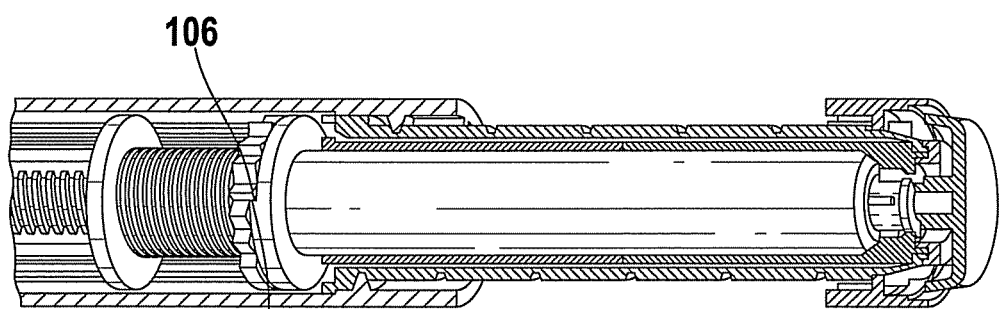
FIG. 13 illustrates a partially cut-away view of the drug delivery device of FIG. 1 in the fourth, final dose dialed, position.

Returning to the drug delivery device 1 illustrated in FIGS. 1-5, when the final dose dispensed position (See, e.g., FIGS. 4, 5 and 13) is reached, a radial stop 106 formed on a second surface of the part nut 40 abuts a radial stop 108 on a first surface of the second flange 34 of the drive sleeve 30, preventing both the nut 40 and the drive sleeve 30 from rotating further. In an alternative arrangement, a first surface of the part nut 40 may be provided with a radial stop for abutment with a radial stop provided on a second surface of the first flange 32. This aids location of the nut 40 at the cartridge full position during assembly of the drug delivery device.

Should a user inadvertently dial beyond a desired dosage, the drug delivery device of FIG. 9 allows the dosage to be dialed down without dispense of medicinal product from the cartridge (See, e.g., FIG. 10). For example, as illustrated in FIG. 15, a user has set a dose of 30 units. However, the user may now want to dial this dosage down without dispensing the previously set 30 Unit dose. In this arrangement, in order for the user to dial down the dosage, the dose dial sleeve 70 is rotated in a direction towards the user and the dose dial grip 76 is counter rotated (See, e.g., arrow B in FIG. 10). This causes the system to act in reverse. The flexible arm 52 preventing the clicker 50 from rotating. The torque transmitted through the clutch 60 causes the saw teeth 56, 66 to ride over one another to create the clicks corresponding to dialed dose reduction. Preferably the saw teeth 56, 66 are so disposed that the circumferential extent of each saw tooth corresponds to a unit dose.

When the desired dose has been dialed, the user may then dispense this dose by depressing the button 82 (See, e.g., FIG. 11). As the user depresses the button 82 as illustrated in FIG. 11 and FIG. 18, this displaces the clutch 60 axially with respect to the dose dial sleeve, 70 causing the dog teeth 65 to disengage. However the clutch 60 remains keyed in rotation to the drive sleeve 30. The dose dial sleeve 70 and associated dose dial grip 76 are now free to rotate (guided by the helical rib 46 located in helical groove 74).

The axial movement deforms the flexible arm 52 of the clicker 50 to ensure the saw teeth 56, 66 cannot be overhauled during dispense. This prevents the drive sleeve 30 from rotating with respect to the main housing 4 though it is still free to move axially with respect thereto. This deformation is subsequently used to urge the clicker 50, and the clutch 60, back along the drive sleeve 30 to restore the connection between the clutch 60 and the dose dial sleeve 70 when pressure is removed from the button 82. The longitudinal axial movement of the drive sleeve 38 causes the piston rod 20 to rotate 5 though the opening 18 in the insert 16, thereby to advance the piston 18 in the cartridge 8.

Figure 19:
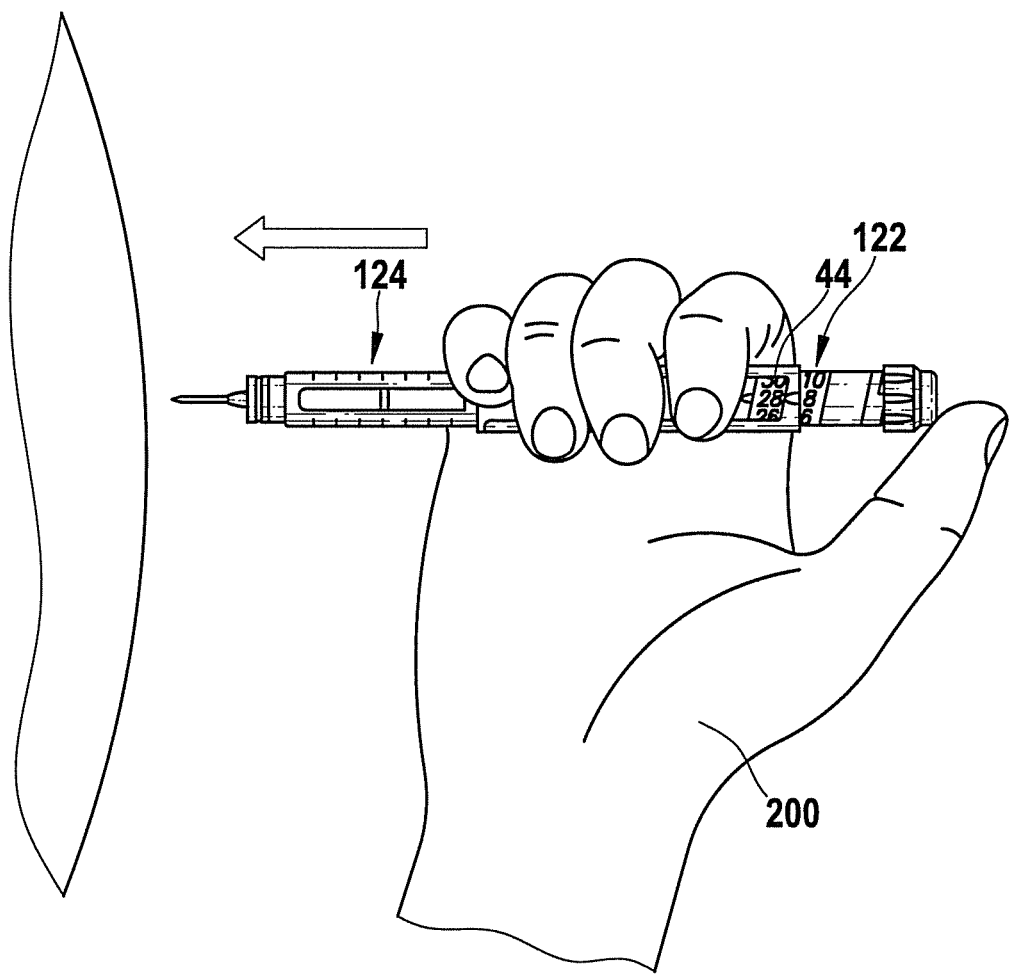
FIG. 19 illustrates how a right handed user would inject a dose with the drug delivery device illustrated in FIG. 1.

As can be seen from FIG. 19, as the user uses his or her right hand 200 to depress the button 82, the user can monitor the dosage being dispensed by way of the scale arrangement 122 viewable via window 44. In addition, as the user uses his or her right hand to depress the button 82 while administering the dose, other labeling 124 provided along the housing (See, e.g., FIG. 15) may also be visible.

Figure 16:
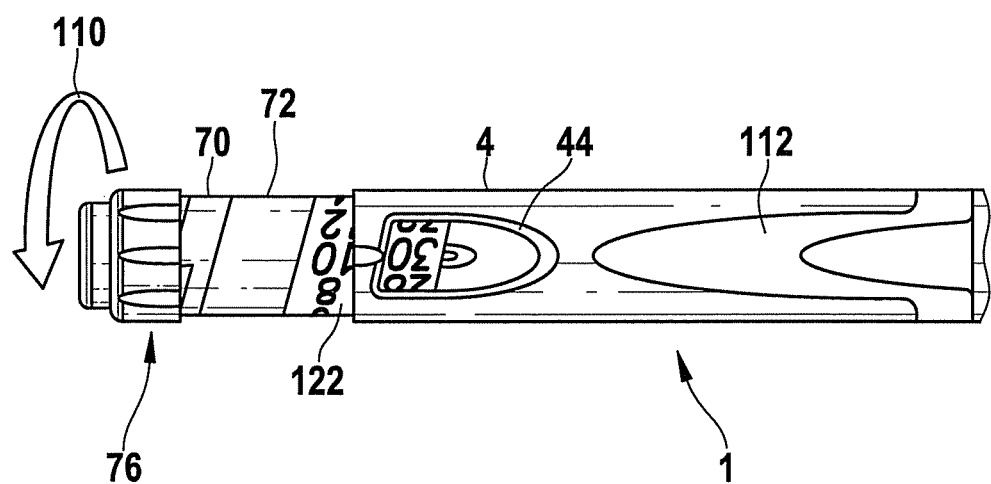
FIG. 16 illustrates how a left handed user would set a dose with the drug delivery device of FIG. 1.

It will be appreciated, however, that if a left handed user (i.e., a left handed diabetic) were to use his or her left hand to first set a dose and then second to administer this previously set dose, neither of these events would occur. For example, FIG. 16 illustrates what would occur if a left handed user were to set a dose the drug delivery device illustrated in FIGS. 1-5. First, the left handed user would use his or her right hand to hold the drug delivery housing 4 and then turn the dose dial grip 76 with the user's left hand. In this orientation, the dose dial grip 76 must be rotated towards the user to set a dose rather than away from the user as with right handed drug delivery devices. In FIG. 16, this is represented by the arrow 110. In such an event, both the scale arrangement 122 provided on the dose dial sleeve 70 and the labeling 112 would be inverted: they would be upside down rather than right side up as illustrated in FIG. 16. Therefore, for left handed users of the drug delivery device, both the scale provided on the dose dial sleeve as well as the labeling 112 must be modified so as to provide a readable scale and readable labeling for those left handed users.

Figure 21:
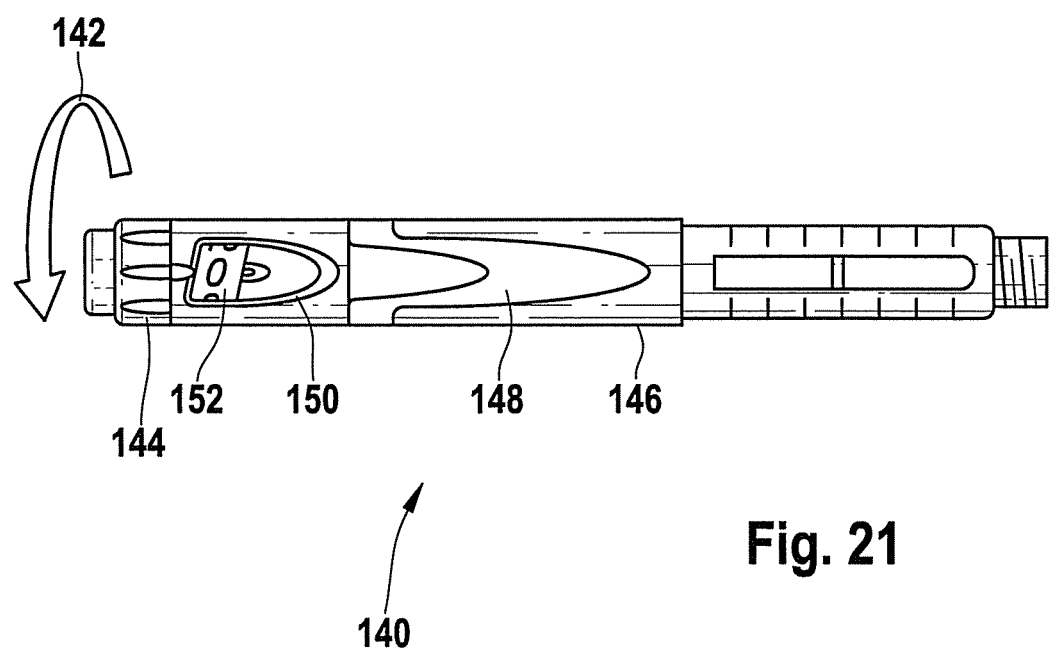
FIG. 21 illustrates how a left handed user would set a dose with an alternative drug delivery device.

FIG. 21 illustrates an alternative drug delivery device 140 wherein a dose may be selected by a left handed user by rotating the dose dial grip 144 in a direction of arrow 142: that is, rotation of the dose dial grip 144 towards the user. In this arrangement, the user holds the housing 146 in their right hand. Then, the user can use his or her left hand to set a dose via dose dial grip 142. As the user sets the dose, an alternative scale arrangement 152 must be provided so that the user can view the scale arrangement 152 by way of the drug delivery device window 150 in a right side up orientation, rather than the inverted scale 122 illustrated with the device 1 in FIG. 16. To provide a viewable scale that is readable and not inverted in this configuration, a modified scale from that provided in FIG. 17 must be provided.

Figure 22:
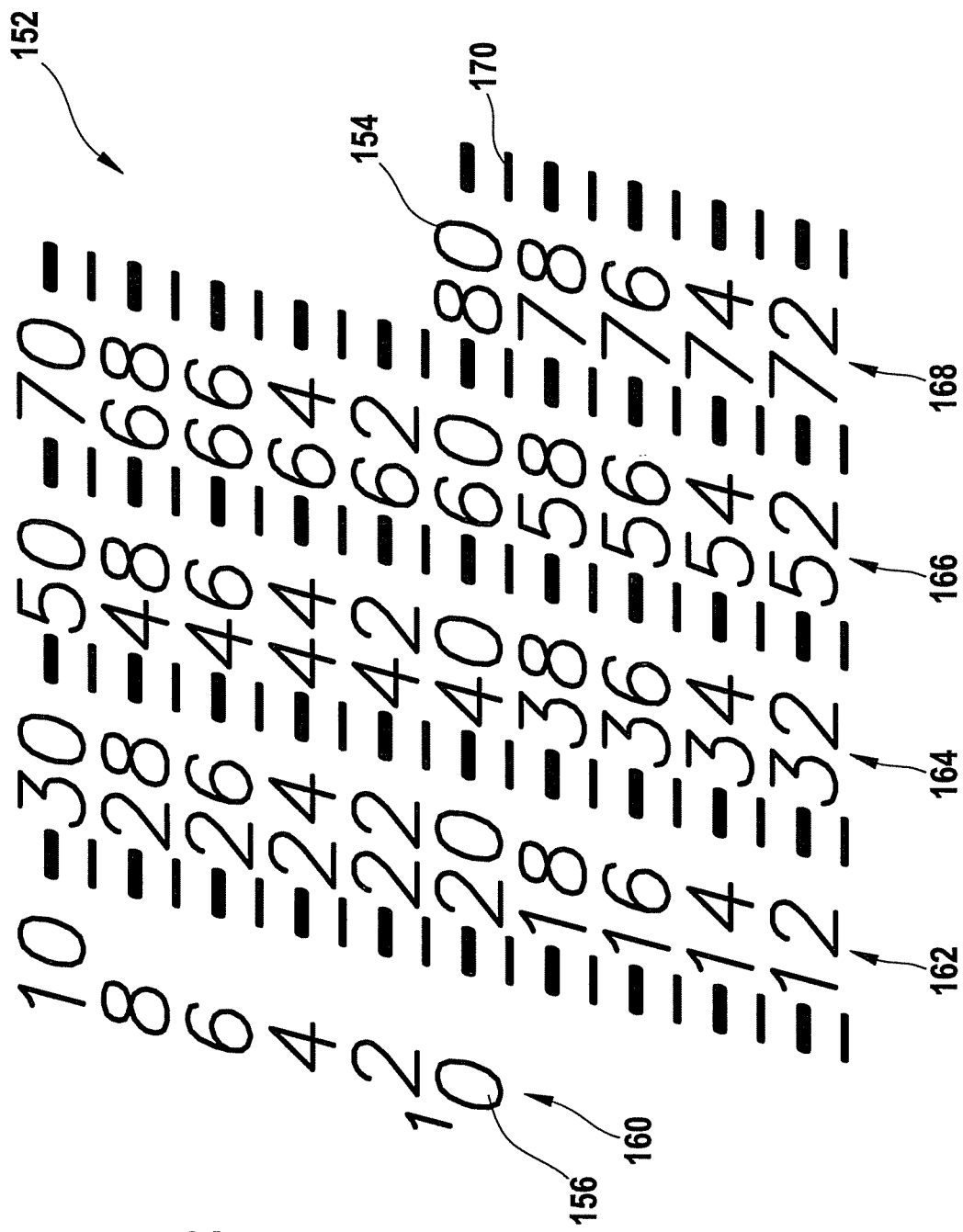
FIG. 22 illustrates an alternative scale arrangement that might be used for the alternative drug delivery device of FIG. 20.

FIG. 22 illustrates one arrangement of an alternative scale arrangement 152 that could be provided along an outer surface of a dose dial sleeve in drug delivery device 140 of FIG. 21. The general construction of the alternative arrangement of the drug delivery device 140 along with its dose setting mechanism provided in FIG. 21 is essentially identical to the general construction and operation of the drug delivery device 1 illustrated in FIG. 1-5. However, both the alternative scale arrangement 152 and alternative labeling 148 have been modified from the scale arrangement 122 and labeling 112 of device 1 illustrated in FIG. 20. In this alternative configuration, when a left handed user sets a dose, both the scale 152 and label 148 may be viewed in a correct orientation: where the scale and label are right side up and not inverted.

FIG. 22 illustrates one arrangement for such a modified scale 152. As may be seen from this alternative scale arrangement, again five columns of reference numerals are provided: a first column 160, a second column 162, a third column 166, a fourth column 166, and a fifth column 168. As can be seen from the first scale arrangement 122 illustrated in 17, the orientation of the five columns of the alternative scale arrangement 152 has been alternated from the scale arrangement provided in FIG. 17.

Scale arrangement 152 comprises a maximum scale reference numeral "80" 154 and a minimum scale reference numeral "0" 156. Similar to the scale arrangement provided in FIG. 17, the maximum scale reference numeral 154 is indicative of a maximum dose settable by the drug delivery device 140 and is "80" Units. Between the maximum and minimum reference numerals, other doses are noted in increments of 2: (e.g., 2, 4, 6, 8 etc.) Again, single unit doses and odd unit doses are also provided by way of the hash marks provided between even numbered reference numerals. For example, hash mark 170 indicates a 79 Unit dose, a dose between the maximum dose "80" Units and a dose of 78 Units.

Unlike the scale arrangement 122 of FIG. 17, however, in the alternative scale arrangement 152, the reference numeral column containing the maximum settable dose "80" Units is provided along a right hand of the scale arrangement while the minimum dose "0" Units is now provided in the fifth scale arrangement column 168 provided at a left hand of the arrangement. Another difference between the modified scale arrangement 152 and the scale arrangement 122 provided in FIG. 17 is that in the modified scale arrangement 152, the dose setting numerals increase from a bottom of a column to a top of a column. For example, in the first column 160 of scale arrangement 152, the dose will increase from the minimum "0," 2, 4, and so on. Consequently, if modified scale arrangement 152 were to be provided on the dose dial sleeve of a drug delivery device 140 as illustrated in FIG. 22, the higher dose numerals 154 would reside along the distal end of the dose dial sleeve while the lower dose numerals would reside along a proximal end of the dose dial sleeve 70. Consequently, as a user rotates the dose dial sleeve by way of the dose dial grip 76 in a direction towards the user with the user's left hand, the dose dial sleeve 70 would extend out of the housing and the scale arrangement 152 could be read from the right side up scale in viewable window 44 and would no longer be inverted as illustrated in FIG. 16.

Figure 23:
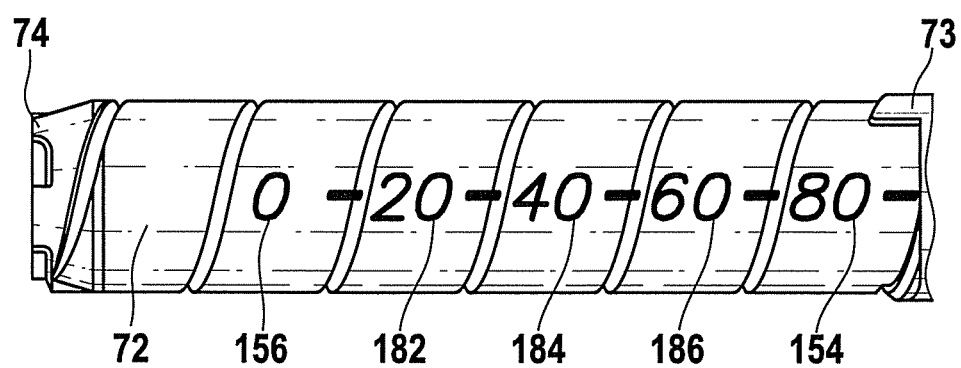
FIG. 23 illustrates the alternative scale arrangement of FIG. 22 provided along an outer surface of a dose dial sleeve.

FIG. 23 illustrates the scale arrangement of FIG. 18 provided along an outer surface 72 of the dose dial sleeve 70. As can be seen from FIG. 18, scale arrangement 122 has the maximum settable dose value "80" provided at the distal end 73 and the minimum settable dose value "0" provided at the proximal end 74 of the dose dial sleeve 70. Intermittent scale numerals "60" Units 186, "40" Units 184 and "20" Units 182 are also provided but their relative location along the outer surface 72 of the dose dial sleeve has been modified as compared to FIG. 18.

Figure 20:
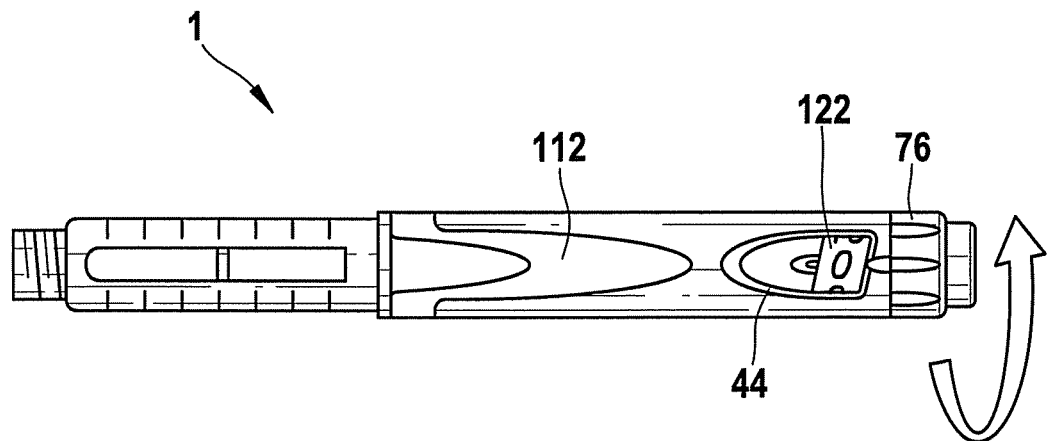
FIG. 20 illustrates how a right handed user would set a dose with the drug delivery device of FIG. 1.

Another modification that can be made to the drug delivery device 140 of FIG. 21 from the drug delivery device 1 illustrated in FIG. 20 is that an orientation of label 148 has changed. Now, with the drug delivery device 140 of FIG. 21, as a user holds the device housing 4 in their right hand and sets a dose with their left hand by turning the dose dial grip in the direction of arrow 142, the left handed user can now view the label in a right side up manner. That is, the label 148 is no longer inverted.

Exemplary embodiments of the present drug delivery device have been described. Those skilled in the art will understand, however, that changes and modifications may be made to these embodiments without departing from the true scope and spirit of the presently proposed drug delivery device, which is defined by the claims.

We claim:
1. A drug delivery device, said device comprising:
a drug delivery device housing;
a medicament contained in said drug delivery device housing;
a dose dial sleeve comprising a scale arrangement that is provided for setting a dose, said dose dial sleeve positioned radially inward of said drug delivery device housing and in threaded engagement with said drug delivery device housing;
a piston rod comprising a first end and a second end, a first helical groove extending from the first end allowing a helical movement of the piston rod with respect to the housing, and a second helical groove extending from the second end and having a same lead as a threaded engagement of the dose dial sleeve with the housing; and
a drive sleeve comprising a helical groove engaging the second helical groove of the piston rod, the drive sleeve being prevented from rotating with respect to the housing during drug delivery;
a dose dial sleeve comprising a scale arrangement that is provided for setting a dose, said dose dial sleeve positioned radially inward of said drug delivery device housing and in threaded engagement with said drug delivery device housing,
the dose dial sleeve and the drive sleeve being releasably rotationally locked to one another for dialing a dose;
said dose dial sleeve rotatable out of said drug delivery device housing so that said scale arrangement is rotated to set a dose of said medicament contained in said drug delivery device;
wherein said dose may be increased by turning said dose dial sleeve in a direction clockwise in relation to a longitudinal axis of the drug delivery device when viewed from a position looking from a proximal end of the drug delivery device to a distal end of the drug delivery device along the longitudinal axis;
wherein said scale arrangement comprises a plurality of numerical values representative of said dose, the plurality of numerical values being helically arranged,
wherein said plurality of numerical values increase from a minimum value near a proximal end of said dose dial sleeve to a maximum value near a distal end of said dose dial sleeve,
wherein, when a user reads said plurality of numerical values from left to right along a surface of said dose dial sleeve from said proximal end of said dose dial sleeve to said distal end of said dose dial sleeve, said plurality of numerical values increase, are in a normal vertically readable orientation and are not inverted,
wherein said plurality of numerical values increase when said dose dial sleeve is turned in the clockwise direction;
wherein said dose dial sleeve translates out of said drug delivery device housing during a dose setting operation; and
wherein said dose dial sleeve translates back into said drug delivery device housing during dose administration.

2. The invention of claim 1 wherein said dose of said medicament may be decreased by rotating said dose dial sleeve in a direction counter-clockwise in relation to a longitudinal axis of the drug delivery device when viewed from a position looking from a proximal end of the drug delivery device to a distal end of the drug delivery device along the longitudinal axis.

3. The invention of claim 1 wherein said drug delivery device housing further comprises a label, said label representative of said medicament contained in said drug delivery device, said label comprising non-inverted text and readable by said user as said user sets said dose of medicament, wherein the non-inverted text is in a normal vertically readable orientation when a user reads said non-inverted text from left to right along the drug delivery device housing from a proximal end of said drug delivery device housing to a distal end of said drug delivery device housing.

4. The invention of claim 1 wherein said drug delivery device housing further includes a viewing window such that during said dose setting operation, said scale arrangement representative of said dose is viewable through said viewing window.

5. The invention of claim 1 wherein said drug delivery device is a disposable drug delivery device.

6. The invention of claim 1 wherein said drug delivery device is a reusable drug delivery device.

7. The invention of claim 1 wherein when said user injects said dose, said dose dial sleeve rotates back into said drug delivery device housing and in a direction counter-clockwise in relation to a longitudinal axis of the drug delivery device when viewed from a position looking from a proximal end of the drug delivery device to a distal end of the drug delivery device along the longitudinal axis.

8. The invention of claim 1 wherein said medicament contained in said drug delivery device is insulin.

9. The invention of claim 8 wherein said insulin comprises a long acting insulin.

10. The invention of claim 1 wherein said medicament contained in said drug delivery device is contained in a cartridge.

11. The invention of claim 10 wherein said cartridge is a removable cartridge.

12. The invention of claim 1 further comprising a colored portion, said colored portion indicating that said user sets said dose of medicament of said drug delivery device by rotating said dose dial sleeve in the direction clockwise in relation to the longitudinal axis.

13. The invention of claim 12 wherein said colored portion is provided on a label.

14. The invention of claim 12 wherein said colored portion is provided on said drug delivery device housing.

15. A pen type drug delivery device comprising:
a drug delivery device housing, said drug delivery device housing having a distal end for mounting a needle assembly and a proximal end;
a dose dial grip;
a cartridge contained in said drug delivery device housing, said cartridge containing a medication;
a dose dial sleeve comprising a scale and situated radially inward of said drug delivery device housing;
a piston rod comprising a first end and a second end,
a first helical groove extending from the first end allowing a helical movement of the piston rod with respect to the housing, and
a second helical groove extending from the second end and having a same lead as a threaded engagement of the dose dial sleeve with the housing;
a drive sleeve comprising a helical groove engaging the second helical groove of the piston rod, the drive sleeve being prevented from rotating with respect to the housing during drug delivery;
a dose dial sleeve comprising a scale and situated radially inward of said drug delivery device housing, the dose dial sleeve and the drive sleeve being releasably rotationally locked to one another for dialing a dose;

said dose dial sleeve threaded and rotatably mounted in said drug delivery device housing and operatively coupled to said dose dial grip, such that said dose dial grip may be rotated in a direction towards a user and clockwise in relation to a longitudinal axis of said pen type drug delivery device when viewed from a proximal end of the drug delivery device housing along a longitudinal axis to a distal end of the drug delivery device housing, a user of said pen type drug delivery device can set a dose of said medication such that, wherein as said dose dial grip is rotated, both said dose dial grip and said dose dial sleeve translate away from said proximal end of said drug delivery device housing, and the scale viewable in a window of said drug delivery device housing in a non-inverted orientation, said scale representative of said dose set by said user, wherein said dose dial sleeve rotates back into said drug delivery device housing during dose injection, and wherein said scale comprises a plurality of numerical values representative of said dose set by said user, the plurality of numerical values being helically arranged, wherein the scale is provided for setting a dose, wherein said plurality of numerical values increase from a minimum value near a proximal end of said dose dial sleeve to a maximum value near a distal end of said dose dial sleeve, wherein, when a user reads said plurality of numerical values from left to right along a surface of said dose dial sleeve from said proximal end of said dose dial sleeve to said distal end of said dose dial sleeve, said plurality of numerical values increase, are in a normal vertically readable orientation and are not inverted, wherein said plurality of numerical values increase when said dose dial grip is turned in the clockwise direction.

16. The invention of claim 15 wherein said dose may be decreased by turning said dose dial grip in a counter-clockwise direction.

17. The invention of claim 15 wherein during an injection of said set dose, said dose dial sleeve rotates back into said proximal end of said drug delivery device housing and rotates in a counter-clockwise direction.

18. The invention of claim 17 wherein during said injection of said set dose, said scale is viewable in the window of said drug delivery device housing.

19. The invention of claim 15 wherein said drug delivery device housing further comprises a label, said label comprising text that is viewable by said user in a normal vertically readable and non-inverted orientation as said user sets said dose of medication and when a user reads said text from left to right along the drug delivery device housing from the proximal end of said drug delivery device housing to the distal end of said drug delivery device housing.

20. A drug delivery device, comprising:
a housing having a distal end provided for mounting a needle assembly and a proximal end;
a dose setting mechanism arranged in the housing;
a dose dial sleeve of the dose setting mechanism, the dose dial sleeve being in threaded engagement with the housing and comprising a scale arrangement;
a piston rod comprising a first end and a second end,
a first helical groove extending from the first end allowing a helical movement of the piston rod with respect to the housing, and
a second helical groove extending from the second end and having a same lead as a threaded engagement of the dose dial sleeve with the housing;
a drive sleeve comprising a helical groove engaging the second helical groove of the piston rod, the drive sleeve being prevented from rotating with respect to the housing during drug delivery;
a dose dial sleeve of the dose setting mechanism, the dose dial sleeve being in threaded engagement with the housing and comprising a scale arrangement,
the dose dial sleeve and the drive sleeve being releasably rotationally locked to one another for dialing a dose;
wherein said scale arrangement comprises a plurality of numerical values representative of a dose, the plurality of numerical values being helically arranged, wherein the scale arrangement is provided for setting a dose,
wherein said plurality of numerical values progress from a first value near a proximal end of said dose dial sleeve to a second value near a distal end of said dose dial sleeve, wherein, when a user reads said plurality of numerical values from left to right along a surface of said dose dial sleeve from said proximal end of said dose dial sleeve to said distal end of said dose dial sleeve, said plurality of numerical values progress, are in a normal vertically readable orientation and are not inverted, wherein said plurality of numerical values progress when said dose dial sleeve is turned in the clockwise direction;
a dose dial grip coupled to the dose dial sleeve, the dose dial grip projecting from the proximal end; and
a window in the housing showing part of the scale arrangement.

21. The drug delivery device according to claim 20, wherein
the scale arrangement comprises a helical column of numerals arranged in a sequence progressing from left to right when a user reads said plurality of numerical values from left to right along a surface of said dose dial sleeve from said proximal end of said dose dial sleeve to said distal end of said dose dial sleeve.

* * * * *